United States Patent [19]

Samejima et al.

[11] Patent Number: 4,670,261
[45] Date of Patent: Jun. 2, 1987

[54] PARENTERAL ALIMENTATION SOLUTION

[75] Inventors: Masayoshi Samejima, Minoh; Saburo Matsuda, Kyoto; Toshio Wakabayashi, Tama; Naoki Hayakawa, Kashiwa, all of Japan

[73] Assignees: Tanabe Seiyaku Co., Ltd., Osaka; Terumo Kabushiki Kaisha, Tokyo, both of Japan

[21] Appl. No.: 779,444

[22] Filed: Sep. 24, 1985

[30] Foreign Application Priority Data

Sep. 25, 1984 [JP] Japan .................................. 59-201066

[51] Int. Cl.$^4$ .................. A61K 31/70; A61K 31/195; A61K 33/00; A61K 33/06; A61K 33/14
[52] U.S. Cl. .................................... 424/127; 424/153; 424/154; 514/23; 514/561
[58] Field of Search ....................... 424/127, 153, 154; 514/23, 561

[56] References Cited

U.S. PATENT DOCUMENTS 4,434,160  2/1984  Jeretin et al. ..................... 514/23
4,438,144  3/1984  Blackburn ......................... 514/561

FOREIGN PATENT DOCUMENTS 0013962  8/1980  European Pat. Off. .
0034034  8/1981  European Pat. Off. .
0144051  6/1985  European Pat. Off. .

Primary Examiner—Stanley J. Friedman
Attorney, Agent, or Firm—Birch, Stewart, Kolasch & Birch

[57] ABSTRACT

A parenteral alimentation solution having excellent nutritional properties with preventing problems such as browning which comprises three components of a reducing sugar, amino acids and electrolytes in a specific composition and a specific amount.

19 Claims, No Drawings

PARENTERAL ALIMENTATION SOLUTION

FIELD OF THE INVENTION

The present invention relates to a novel parenteral alimentation solution. More particularly, it relates to a parenteral alimentation solution having excellent nutritional properties and also containing a reducing sugar as a physiological energy source, an amino acid mixture as a nitrogen source and electrolytes as essential nutrients.

BACKGROUND OF THE INVENTION

Up to now, any parenteral alimentation solution which contains a reducing sugar as well as essential and non-essential amino acids and which further contains electrolytes essential for the living body such as sodium, potassium, phosphorus, magnesium, chlorine and the like has not been put to practical use. For example, although an amino acid infusion solution containing electrolytes has been known, no reducing sugar is contained therein and, in an infusion solution containing both amino acids and a reducing sugar, only sodium and chlorine are present as electrolytes [IYAKUHIN KENKYU, 12, (1), 91-111 (1981)]. In addition, these sodium and chlorine are not intentionally added to an infusion solution but they are inevitably derived from an amino acid component used. For example, when an amino acid is used in the form of its hydrochloride, chlorine is derived therefrom and, when an amino acid hydrochloride is neutralized, sodium is derived therefrom.

In addition to difficulty of determination of an optimum composition, a parenteral alimentation solution containing a reducing sugar, amino acids and electrolytes which are essential nutrients has not been hitherto put to practical use because it is not possible to overcome such a technical difficulty that the alimentation solution turns brown (so-called, browning) due to Maillard reaction of a reducing sugar, for example, glucose with an amino acid during heat sterilization or storage and that browing due to the amino acid and glucose is accelerated and increased in the presence of electrolytes [The Journal of Nutrition, 112, 1631-1637 (1982)]. Thus, in order to prevent such browning, it has been proposed to reduce amounts of electrolytes and further to use L-tryptophan and L-proline which are said to be mainly responsible for browning [The Journal of Nutrition, 112, 1634 (1982)] in their N-acylated forms [Japanese Patent Laid Open Publication No. 115909/1976; and Shinyaku to Rinsho, 29, 305 (1980)].

However, even if it is possible to prevent browning of an infusion solution by using L-proline and L-tryptophan in their N-acylated forms, it is hard to say that N-acylated forms of L-proline and L-tryptophan are most suitable for the living body because these N-acylated amino acids per se are non-physiological amino acids. In addition, as electrolytes, only sodium and chlorine are contained in the infusion solution prepared according to such a known method, but other electrolytes essential to the living body such as potassium, magnesium, phosphorus, etc. are not contained therein.

Accordingly, up to now, in practice, an electrolyte infusion solution and an amino acid-reducing sugar infusion solution has been admixed just prior to administration or they have been separately administered. However, when admixing these solutions, it is necessary to control the pH and osmotic pressure of the resulting mixture suitable for a patient to be administered because they are different from those of the original solutions as prepared and, in addition, there is a problem that the amounts of sodium and chlorine in the mixture should be calculated so as to avoid administration of excess amounts of sodium and chlorine to a patient, when the solutions contain sodium and chlorine. Further, when the solutions are admixed, the possibility of contamination with various microorganisms is increased. In case of administering both solutions separately and successively, a long infusion time is required, which causes pain to a patient for a long time. Further, there is a problem in that a sufficient nutritional effect cannot be expected because each electrolyte which is necessary for an amino acid metabolism is not infused at the same time of infusion of the amino acid.

Thus, in this field of the art, it has been strongly desired to develop a parenteral alimentation solution in which amino acids per se are used without any modification and a reducing sugar and electrolytes are added, in addition, browning due to Maillard reaction is prevented.

OBJECTS AND SUMMARY OF THE INVENTION

The present inventors have intensively studied to solve the above problems. As a result, it has been found that a parenteral alimentation solution showing excellent nutritive effect and at the same time causing no substantial browing can be obtained by balancing the ratio of three components of the composition, i.e., a reducing sugar, physiological amino acids and electrolytes within a specific range.

The main object of the present invention is to provide a parenteral alimentation solution which contains a reducing sugar, physiological amino acids and electrolytes and is substantially prevented from browning.

This object as well as other objects and advantages of the present invention will become aparent to those skilled in the art from the following description.

According to the present invention, there is provided a parenteral alimentation solution which comprises a reducing sugar, physiological amino acids and electrolytes in the composition and the amount shown in Table 1.

TABLE 1

| Components | Amount |
|---|---|
| Sugar | g/l |
| Reducing sugar | 30-150 |
| Physiological amino acids | mg/l |
| L-Isoleucine | 2100-2810 |
| L-Leucine | 3340-4460 |
| L-Valine | 2220-2970 |
| L-Methionine | 960-1290 |
| L-Cysteine | 0-1000 |
| L-Cystine | 0-200 |
| L-Phenylalanine | 1900-2540 |
| L-Tyrosine | 0-1000 |
| L-Tryptophan | 390-530 |
| L-Lysine | 1980-2640 |
| L-Threonine | 1180-1580 |
| L-Arginine | 2740-3660 |
| L-Histidine | 1160-1550 |
| L-Alanine | 2120-2840 |
| L-Aspartic acid | 120-220 |
| L-Glutamic acid | 0-170 |
| Glycine | 1360-1820 |
| L-Proline | 1580-2110 |
| L-Serine | 1030-1390 |
| Electrolytes | mmol/l |
| Sodium | 25-60 |

TABLE 1-continued

| Components | Amount |
| --- | --- |
| Chlorine | 35–65 |
| Potassium | 10–40 |
| Magnesium | 0–5 |
| Phosphorus | 0–10 |

(Provided that all or a part of cysteine and/or cystine may be replaced by methionine, and all or a part of tyrosine may be replaced by phenylalanine.)

The parenteral alimentation solution of the present invention is prepared by admixing the above components in distilled water for infusion, filtering the resulting mixture and sterilizing the mixture.

DETAILED DESCRIPTION OF THE INVENTION

The parenteral alimentation solution of the present invention which has the above composition and contains the above component in the amount as shown in Table 1 can be administered to a human patient by various routes (e.g. peripheral intravenous administration, central intravenous administration) according to a desired purpose. Particularly, the parenteral alimentation solution of the present invention has a composition suitable for peripheral intravenous administration. Additionally, the parenteral alimentation solution shows excellent nutritional effect because it has such novel characteristics that it contains all three essential components, i.e., a reducing sugar which is a physiological energy source, a well-balanced amino acid mixture which is a physiological nitrogen source and electrolytes essential for the living body in a stable state. For example, a reducing sugar is most readily metabolized as an energy source and effectively utilized and it makes utilization of the other component, amino acids, in a protein synthesis possible. Further, the parenteral alimentation solution of the present invention has such characteristics that, in view of the feature of amino acid metabolism in nutrition via a vein, the amino acid composition has such a high branched-chain amino acid content as 29–33% (w/w) based on the weight of the total amino acids with maintaining balance of amino acid composition such as the ratio of total amino acids and essential amino acids, the ratio of essential amino acids and non-essential amino acids or the like and that the solution contains sufficient other nutritive amino acids. In addition, with regard to the electrolyte composition, the parenteral alimentation solution of the present invention has such characteristics that it contains electrolytes in an amount just enough to maintain nutrition. As a preferred aspect of the composition of the parenteral alimentation solution of the present invention having the above characteristics, there can be exemplified the solution having the following composition of a reducing sugar, amino acids and electrolytes.

| Sugar | g/l |
| --- | --- |
| Reducing sugar | 30–150 |
| Physiological amino acids | mg/l |
| L-Isoleucine | 2100–2810 |
| L-Leucine | 3340–4460 |
| L-Valine | 2220–2970 |
| L-Methionine | 960–1290 |
| L-Cysteine | 0–1000 |
| L-Cystine | 0–200 |
| L-Phenylalanine | 1900–2540 |
| L-Tyrosine | 0–1000 |
| L-Tryptophan | 390–530 |
| L-Lysine | 1980–2640 |
| L-Threonine | 1180–1580 |
| L-Arginine | 2740–3660 |
| L-Histidine | 1160–1550 |
| L-Alanine | 2120–2840 |
| L-Aspartic acid | 120–170 |
| L-Glutamic acid | 120–170 |
| Glycine | 1360–1820 |
| L-Proline | 1580–2110 |
| L-Serine | 1030–1390 |
| Electrolytes | mmol/l |
| Sodium | 25–60 |
| Chlorine | 35–65 |
| Potassium | 10–40 |
| Magnesium | 0–5 |
| Phosphorus | 0–10 |

(Provided that all or a part of cysteine and/or cystine may be replaced by methionine, and all or a part of tyrosine may be replaced by phenylalanine.)

As another preferred aspect of the composition of the parenteral alimentation solution of the present invention having the above characteristics, there can be exemplified the solution having the following composition of a reducing sugar, amino acids and electrolytes.

| Reducing sugar | g/l |
| --- | --- |
| glucose | 71–79 |
| Amino acids | mg/l |
| L-Isoleucine | 2220–2460 |
| L-Leucine | 3520–3900 |
| L-Valine | 2350–2600 |
| L-Methionine | 1010–1420 |
| L-Phenylalanine | 2010–2230 |
| L-Tyrosine | 130–150 |
| L-Tryptophan | 410–470 |
| L-Lysine | 2090–2310 |
| L-Threonine | 1250–1390 |
| L-Arginine | 2890–3210 |
| L-Histidine | 1220–1360 |
| L-Alanine | 2240–2490 |
| L-Aspartic acid | 130–170 |
| L-Glutamic acid | 0–150 |
| Glycine | 1430–1590 |
| L-Proline | 1670–1850 |
| L-Serine | 1090–1220 |
| Electrolytes | mmol/l |
| Sodium | 25–35 |
| Chlorine | 45–55 |
| Potassium | 20–30 |
| Magnesium | 1.5–2.5 |
| Phosphorus | 1.5–2.5 |

(Provided that, if necessary, L-cysteine and/or L-cystine may be further added to the above composition in an amount of 260–290 mg/l.)

In the parenteral alimentation solution of the present invention, the reducing sugar used in not limited to a specific one so far as it can be metabolized and utilized as an energy source in the living body. However, glucose and maltose are preferable and they may be used alone or in a combination thereof.

The amino acid used in the parenteral alimentation solution of the present invention may be either in the free acid form or in the form of a salt thereof with a metal such as potassium or sodium, a mineral acids such as sulfuric acid or hydrochloric acid, or an organic acid such as acetic acid or maleic acid. Further, the amino acid may be in the form of a salt with another amino acid, a peptide and the like. In the amino acid composition of the alimentation solution of the present invention, all or a part of L-cysteine and/or L-cystine can be replaced by L-methionine because, as a sulfur containing amino acid, L-cysteine and L-cystine are nutritionally equivalent to L-methionine. Likewise, all or a part of tyrosine which is an aromatic amino acid can be replaced by L-phenylalanine.

Further, as the electrolytes used in the alimentation solution fluid of the present invention, there can be used as a sodium source a commonly used sodium compound such as sodium hydroxide, sodium chloride, a sodium salt of an organic acid, a sodium salt of an amino acid, etc.; as a chlorine source hydrochloric acid, sodium chloride, potassium chloride, a hydrochloride of an amino acid, etc.; as a potassium source potassium hydroxide, potassium chloride, a potassium salt of an organic acid, a potassium salt of an amino acid, etc.; and as a magnesium source magnesium chloride, magnesium sulfate, a magnesium salt of an organic acid, a magnesium salt of an amino acid, etc. As a source for phosphorus, sodium and potassium, there can also be used disodium monohydrogen phosphate, sodium dihydrogen phosphate, potassium monohydrogen phosphate, dipotassium dihydrogen phosphate, etc. The concentrations of the above reducing sugar, amino acids and electrolytes in the alimentation solution can be appropriately varied within the range shown in Table 1 according to conditions and age of a patient to be treated, diseases to be treated, etc. The preferred concentration range for the reducing sugar is about 5–9 w/v %, particularly, 6–8 w/v % and, for the amino acids, preferably, the total amino acid concentration range is about 2.5–3.5 w/v %. For the electrolytes, it is preferable that the concentration of sodium ion is 25–35 mmol/l, the concentration of potassium ion is 20–30 mmol/l, the concentration of chlorine ion is 45–55 mmol, the concentration of magnesium ion is 1.5–2.5 mmol/l and the concentration of phosphorus ion is 1.5–2.5 mmol/l. In addition, in view of stabilization of the alimentation solution, it is preferable to adjust each concentration of the reducing sugar and the amino acids so that the product of the concentration (w/v %) of the reducing sugar (as glucose) by that of the total amino acids is 7–25, preferably 12–24, most preferably 17–23 because an excellent stabilization effect can be obtained.

It is preferable to adjust the pH of the parenteral alimentation solution of the present invention to 4.0–6.0. The alimentation solution can further contain other ingredients commonly used in the preparation of an infusion fluid such as a stabilizing agent, an agent for adjusting pH, etc.

The parenteral alimentation solution of the present invention can be prepared according to a conventional technique for the preparation of a conventional infusion solution or injectable preparation by admixing the above components in distilled water for infusion, filtering the resulting mixture and sterilizing the mixture. Filtration can be effected by using a microporous membrane filter such as a Millipore filter. The parenteral alimentation solution of the present invention can be subjected to heat sterilization.

The parenteral alimentation solution of the present invention thus obtained contains all three components of the reducing sugar, the amino acids and the electrolytes and has excellent nutritional properties. Further, in the parenteral alimentation solution of the present invention, although all the amino acids used are physiological amino acids, browning can be prevented without using any nonphysiological amino acid such as N-acetyl-tryptophan. In addition, there is no need to use another infusion solution in combination with the parenteral alimentation solution of the present invention because the latter solution contains substantially all the components considered to be required for a peripheral intravenous infusion solution and, thereby, problems which accompany the use of the other infusion solution (e.g. variation of nature of the resulting mixture, contamination with microorganisms or foreign materials) can be avoided. However, if necessary, a suitable infusion solution may be mixed into the solution of this invention.

The following examples further illustrate the present invention in detail but are not to be construed to limit the scope thereof.

EXAMPLE 1

| Formulation | |
|---|---|
| Components | Amount |
| Glucose | 75 g |
| L-Isoleucine | 2.34 g |
| L-Leucine | 3.71 g |
| L-Valine | 2.48 g |
| L-Methionine | 1.07 g |
| L-Phenylalanine | 2.12 g |
| L-Tyrosine | 0.14 g |
| L-Threonine | 1.32 g |
| L-Alanine | 2.37 g |
| L-Proline | 1.76 g |
| L-Serine | 1.16 g |
| Glycine | 1.51 g |
| L-Aspartic acid | 0.14 g |
| L-Glutamic acid | 0.14 g |
| L-Arginine | 0.78 g |
| L-Arginine hydrochloride | 2.74 g |
| L-Histidine | 1.29 g |
| L-Lysine hydrochloride | 2.75 g |
| L-Cysteine hydrochloride | 0.36 g |
| L-Tryptophan | 0.44 g |
| Sodium lactate | 3.36 g |
| Potassium chloride | 1.27 g |
| Dipotassium monohydrogen phosphate | 0.26 g |
| Magnesium chloride hexahydrate | 0.30 g |
| Sodium hydrogen sulfite | 0.50 g |

The above components were dissolved in 750 ml of distilled water for injection and to the solution was added additional distilled water to bring the total volume of the solution to 1 liter. The solution was filtered through a Millipore filter and distributed in an amount of 200 ml per vial. The vials were sealed and sterilized with heating to obtain the desired parenteral alimentation solution.

Even after sterilization, the alimentation solution thus obtained was colorless and clear and no browning was observed.

EXAMPLE 2

| Formulation | |
|---|---|
| Components | Amount |
| Glucose | 700 g |
| L-Isoleucine | 25.5 g |
| L-Leucine | 40.4 g |
| L-Valine | 27.0 g |
| L-Methionine | 11.7 g |
| L-Phenylalanine | 23.1 g |
| L-Tyrosine | 1.5 g |
| L-Threonine | 14.4 g |
| L-Alanine | 25.8 g |
| L-Proline | 19.2 g |
| L-Serine | 12.6 g |

-continued

| Formulation | |
|---|---|
| Components | Amount |
| Glycine | 16.5 g |
| L-Aspartic acid | 1.5 g |
| L-Glutamic acid | 1.5 g |
| L-Arginine | 33.3 g |
| L-Histidine | 14.1 g |
| L-Lysine hydrochloride | 30.0 g |
| L-Cysteine hydrochloride | 1.3 g |
| L-Tryptophan | 4.8 g |
| Sodium chloride | 17.5 g |
| Potassium chloride | 12.7 g |
| Dipotassium monohydrogen phosphate | 2.6 g |
| Magnesium chloride hexahydrate | 3.0 g |
| Sodium hydrogen sulfite | 5.0 g |

The above components were dissolved in 7 liters of distilled water for injection and to the solution was added additional distilled water to bring the total volume of the solution to 10 liters. The solution was filtered through Millipore filter and distributed in an amount of 500 ml per vial. The vials were sealed and sterilized with heating to obtain the desired parenteral alimentation solution.

Even after sterilization, the alimentation solution thus obtained was colorless and clear and no browning was observed.

EXAMPLE 3

| Formulation | |
|---|---|
| Components | Amount |
| Glucose | 750 g |
| L-Isoleucine | 23.4 g |
| L-Leucine | 37.1 g |
| L-Valine | 24.8 g |
| L-Methionine | 12.8 g |
| L-Phenylalanine | 21.2 g |
| L-Tyrosine | 1.4 g |
| L-Threonine | 13.2 g |
| L-Alanine | 23.7 g |
| L-Proline | 17.6 g |
| L-Serine | 11.6 g |
| Glycine | 15.1 g |
| L-Aspartic acid | 1.4 g |
| L-Glutamic acid | 1.4 g |
| L-Arginine | 29.3 g |
| L-Arginine hydrochloride | 1.5 g |
| L-Histidine hydrochloride monohydrate | 17.4 g |
| L-Lysine hydrochloride | 27.5 g |
| L-Cysteine | 1.0 g |
| L-Tryptophan | 4.8 g |
| Sodium lactate | 33.6 g |
| Potassium chloride | 12.7 g |
| Dipotassium monohydrogen phosphate | 2.6 g |
| Magnesium chloride hexahydrate | 3.0 g |
| Sodium hydrogen sulfite | 5.0 g |

The above components were dissolved in 7 liters of distilled water for injection and to the solution was added additional distilled water to bring the total volume of the solution to 10 liters. The solution was filtered through a Millipore filter and distributed in an amount of 1000 ml per bag made of a soft plastic (crosslinked EVA). The bags were sealed and sterilized with heating to obtain the desired parenteral alimentation solution.

Even after sterilization, the alimentation solution thus obtained was colorless and clear and no browning was observed.

EXAMPLE 4

| Formulation | |
|---|---|
| Components | Amount |
| Maltose | 1000 g |
| L-Isoleucine | 25.5 g |
| L-Leucine | 40.4 g |
| L-Valine | 27.0 g |
| L-Methionine | 11.7 g |
| L-Phenylalanine | 23.1 g |
| L-Tyrosine | 1.5 g |
| L-Threonine | 14.4 g |
| L-Alanine | 25.8 g |
| L-Proline | 19.2 g |
| L-Serine | 12.6 g |
| Glycine | 16.5 g |
| L-Aspartic acid | 1.5 g |
| L-Glutamic acid | 1.5 g |
| L-Arginine | 8.5 g |
| L-Arginine hydrochloride | 30.0 g |
| L-Histidine | 14.1 g |
| L-Lysine hydrochloride | 30.0 g |
| L-Cysteine hydrochloride | 4.0 g |
| L-Tryptophan | 4.8 g |
| Sodium lactate | 33.6 g |
| Potassium chloride | 12.7 g |
| Dipotassium monohydrogen phosphate | 2.6 g |
| Magnesium chloride hexahydrate | 3.0 g |
| Sodium hydrogen sulfite | 5.0 g |

The above components were dissolved in 7.5 liters of distilled water for injection and to the solution was added additional distilled water to bring the total volume of the solution to 10 liters. The solution was filtered through a Millipore filter and distributed in an amount of 1000 ml per bag made of a soft plastic (crosslinked EVA). The bags were sealed and sterilized with heating to obtain the desired parenteral alimentation solution.

Even after sterilization, the alimentation solution thus obtained was colorless and clear and no browning was observed.

EXAMPLE 5

| Formulation | |
|---|---|
| Components | Amount |
| Glucose | 750 g |
| L-Isoleucine | 24.1 g |
| L-Leucine | 38.6 g |
| L-Valine | 25.0 g |
| L-Methionine | 13.7 g |
| L-Phenylalanine | 21.1 g |
| L-Tyrosine | 1.4 g |
| L-Threonine | 13.2 g |
| L-Alanine | 23.7 g |
| L-Proline | 17.0 g |
| L-Serine | 10.3 g |
| Glycine | 15.1 g |
| L-Aspartic acid | 1.4 g |
| L-Glutamic acid | 1.4 g |
| L-Arginine | 29.8 g |
| L-Histidine hydrochloride monohydrate | 17.4 g |
| L-Lysine hydrochloride | 27.5 g |
| L-Tryptophan | 4.4 g |
| Sodium chloride | 0.9 g |
| Potassium chloride | 15.8 g |
| Dipotassium monohydrogen phosphate | 2.6 g |
| Magnesium chloride hexahydrate | 3.0 g |
| Sodium lactate | 28.5 g |
| Lactic acid | 2.25 g |

The above components were dissolved in 7.5 liters of distilled water for injection and to the solution was added additional distilled water to bring the total volume of the solution to 10 liters. The solution was filtered through a Millipore filter and distributed in an amount of 500 ml per vial. The vials were sealed and sterilized with heating to obtain the desired parenteral alimentation solution.

Even after sterilization, the alimentation solution thus obtained was colorless and clear and no browning was observed.

What is claimed is:

1. A parenteral alimentation solution, which comprises: a reducing sugar selected from glucose, maltose and mixtures thereof; physiological amino acids; and electrolytes in the composition and the amount as shown in Table 1:

TABLE 1

| Components | Amount |
|---|---|
| Sugar | g/l |
| Reducing sugar | 30–150 |
| Physiological amino acids | mg/l |
| L-Isoleucine | 2100–2810 |
| L-Leucine | 3340–4460 |
| L-Valine | 2220–2970 |
| L-Methionine | 960–1290 |
| L-Cysteine | 0–1000 |
| L-Cystine | 0–200 |
| L-Phenylalanine | 1900–2540 |
| L-Tyrosine | 0–1000 |
| L-Tryptophan | 390–530 |
| L-Lysine | 1980–2640 |
| L-Threonine | 1180–1580 |
| L-Arginine | 2740–3660 |
| L-Histidine | 1160–1550 |
| L-Alanine | 2120–2840 |
| L-Aspartic acid | 120–220 |
| L-Glutamic acid | 0–170 |
| Glycine | 1360–1820 |
| L-Proline | 1580–2110 |
| L-Serine | 1030–1390 |
| Electrolytes | mmol/l |
| Sodium | 25–60 |
| Chlorine | 35–65 |
| Potassium | 10–40 |
| Magnesium | 0–5 |
| Phosphorus | 0–10 | wherein the product of the concentration (w/v %) of the reducing sugar (as glucose) by that of the total amino acids is 7 to 25.

2. A parenteral alimentation solution according to claim 1, wherein the solution has the following composition:

| Sugar | g/l |
|---|---|
| Reducing sugar | 30–150 |
| Physiological amino acids | mg/l |
| L-Isoleucine | 2100–2810 |
| L-Leucine | 3340–4460 |
| L-Valine | 2220–2970 |
| L-Methionine | 960–1290 |
| L-Cysteine | 0–1000 |
| L-Cystine | 0–200 |
| L-Phenylalanine | 1900–2540 |
| L-Tyrosine | 0–1000 |
| L-Lysine | 1980–2640 |
| L-Threonine | 1180–1580 |
| L-Arginine | 2740–3660 |
| L-Histidine | 1160–1550 |
| L-Alanine | 2120–2840 |
| L-Aspartic acid | 120–170 |
| L-Glutamic acid | 120–170 |
| Glycine | 1360–1820 |
| L-Proline | 1580–2110 |
| L-Serine | 1030–1390 |

| Electrolytes | mmol/l |
|---|---|
| Sodium | 25–60 |
| Chlorine | 35–65 |
| Potassium | 10–40 |
| Magnesium | 0–5 |

3. A parenteral alimentation solution according to claim 1, wherein the concentration of the reducing sugar is about 5–9 w/v%.

4. A parenteral alimentation solution according to claim 3, wherein the concentration of the reducing sugar is 6–8 w/v%.

5. A parenteral alimentation solution according to claim 1, wherein the total amino acid concentration is about 2.5–3.5 w/v%.

6. A parenteral alimentation solution according to claim 1, wherein the concentration of the electrolytes are as follows:

| Sodium | 25–35 | mmol/l |
|---|---|---|
| Potassium | 20–30 | mmol/l |
| Chlorine | 45–55 | mmol/l |
| Magnesium | 1.5–2.5 | mmol/l |
| Phosphorus | 1/5–2.5 | mmol/l |

7. A parenteral alimentation solution according to claim 1, wherein the product is 12–24.

8. A parenteral alimentation solution according to claim 1, wherein the product is 17–23.

9. A parenteral alimentation solution according to claim 1, wherein the pH of the solution is 4.0–6.0.

10. A parenteral alimentation solution according to claim 1 wherein the fluid has the following composition:

| Reducing sugar | g/l |
|---|---|
| glucose | 71–79 |
| Amino acids | mg/l |
| L-Isoleucine | 2220–2460 |
| L-Leucine | 3520–3900 |
| L-Valine | 2350–2600 |
| L-Methionine | 1010–1420 |
| L-Phenylalanine | 2010–2230 |
| L-Tyrosine | 130–150 |
| L-Tryptophan | 410–470 |
| L-Lysine | 2090–2310 |
| L-Threonine | 1250–1390 |
| L-Arginine | 2890–3210 |
| L-Histidine | 1220–1360 |
| L-Alanine | 2240–2490 |
| L-Aspartic acid | 130–170 |
| L-Glutamic acid | 0–150 |
| Glycine | 1430–1590 |
| L-Proline | 1670–1850 |
| L-Serine | 1090–1220 |
| Electrolytes | mmol/l |
| Sodium | .25–35 |
| Chlorine | 45–55 |
| Potassium | 20–30 |
| Magnesium | 1.5–2.5 |
| Phosphorus | 1.5–2.5 |

11. A parenteral alimentation solution according to claim 1, which contains glucose as the reducing sugar.

12. A parenteral alimentation solution according to claim 1, which contains maltose as the reducing sugar.

13. A parenteral alimentation solution according to claim 1, which contains L-cysteine.

14. A parenteral alimentation solution according to claim 1, which contains L-cystine.

15. A parenteral alimentation solution according to claim 1, which contains L-tyrosine.

16. A parenteral alimentation solution according to claim 1, which contains methionine.

17. A parenteral alimentation solution according to claim 1, which contains phenylalanine.

18. A parenteral alimentation solution, consisting essentially of: a reducing sugar selected from glucose, maltose and mixtures thereof; physiological amino acids; and electrolytes in the composition and the amount as shown in Table 1:

TABLE 1

| Components | Amount |
| --- | --- |
| Sugar | g/l |
| Reducing sugar | 30–150 |
| Physiological amino acids | mg/l |
| L-Isoleucine | 2100–2810 |
| L-Leucine | 3340–4460 |
| L-Valine | 2220–2970 |
| L-Methionine | 960–1290 |
| L-Cysteine | 0–1000 |
| L-Cystine | 0–200 |
| L-Phenylalanine | 1900–2540 |
| L-Tyrosine | 0–1000 |
| L-Tryptophan | 390–530 |
| L-Lysine | 1980–2640 |
| L-Threonine | 1180–1580 |
| L-Arginine | 2740–3660 |
| L-Histidine | 1160–1550 |
| L-Alanine | 2120–2840 |
| L-Aspartic acid | 120–220 |
| L-Glutamic acid | 0–170 |
| Glycine | 1360–1820 |
| L-Proline | 1580–2110 |
| L-Serine | 1030–1390 |
| Electrolytes | mmol/l |
| Sodium | 25–60 |
| Chlorine | 35–65 |
| Potassium | 10–40 |
| Magnesium | 0–5 |

TABLE 1-continued

| Components | Amount |
| --- | --- |
| Phosphorus | 0–10 | wherein the product of the concentration (w/v %) of the reducing sugar (as glucose) by that of the total amino acids is 7 to 25.

19. A parenteral alimentation solution, consisting of: a reducing sugar selected from glucose, maltose and mixtures thereof; physiological amino acids; and electrolytes in the composition and the amount as shown in Table 1;

TABLE 1

| Components | Amount |
| --- | --- |
| Sugar | g/l |
| Reducing sugar | 30–150 |
| Physiological amino acids | mg/l |
| L-Isoleucine | 2100–2810 |
| L-Leucine | 3340–4460 |
| L-Valine | 2220–2970 |
| L-Methionine | 960–1290 |
| L-Cysteine | 0–1000 |
| L-Cystine | 0–200 |
| L-Phenylalanine | 1900–2540 |
| L-Tyrosine | 0–1000 |
| L-Tryptophan | 390–530 |
| L-Lysine | 1980–2640 |
| L-Threonine | 1180–1580 |
| L-Arginine | 2740–3660 |
| L-Histidine | 1160–1550 |
| L-Alanine | 2120–2840 |
| L-Aspartic acid | 120–220 |
| L-Glutamic acid | 0–170 |
| Glycine | 1360–1820 |
| L-Proline | 1580–2110 |
| L-Serine | 1030–1390 |
| Electrolytes | mmol/l |
| Sodium | 25–60 |
| Chlorine | 35–65 |
| Potassium | 10–40 |
| Magnesium | 0–5 |
| Phosphorus | 0–10 | wherein the product of the concentration (w/v %) of the reducing sugar (as glucose) by that of the total amino acids is 7 to 25.

* * * * *

UNITED STATES PATENT AND TRADEMARK OFFICE
CERTIFICATE OF CORRECTION

PATENT NO.   :   4,670,261
DATED        :   June 2, 1987
INVENTOR(S)  :   Masayoshi Samejima et al.

It is certified that error appears in the above-identified patent and that said Letters Patent is hereby corrected as shown below:

<u>Claim 2</u>

Below "Magnesium 0-5" please insert the following:

--Phosphorous 0-10--

Signed and Sealed this

Eleventh Day of July, 1989

Attest:

DONALD J. QUIGG

*Attesting Officer*                *Commissioner of Patents and Trademarks*